United States Patent
Chen et al.

(10) Patent No.: US 10,045,962 B2
(45) Date of Patent: Aug. 14, 2018

(54) USES OF DULOXETINE HCL MEDICAMENT IN PREPARING PHARMACEUTICAL TREATMENT OF CANCER

(71) Applicant: LAUNX BIOMEDICAL CO., LTD., Kaohsiung (TW)

(72) Inventors: Chiu-Hung Chen, Kaohsiung (TW); Show-Mei Chuang, Taichung (TW); Tzong-Der Way, Kaohsiung (TW); Nai-Wan Hsiao, Taichung (TW)

(73) Assignee: LAUNX BIOMEDICAL CO., LTD., Kaohsiung (TW)

( * ) Notice: Subject to any disclaimer, the term of this patent is extended or adjusted under 35 U.S.C. 154(b) by 0 days.

(21) Appl. No.: 15/492,859

(22) Filed: Apr. 20, 2017

(65) Prior Publication Data
US 2017/0216247 A1    Aug. 3, 2017

Related U.S. Application Data

(63) Continuation of application No. PCT/CN2015/092782, filed on Oct. 23, 2015.

(60) Provisional application No. 62/068,298, filed on Oct. 24, 2014.

(51) Int. Cl.
*A61K 31/38* (2006.01)
*A61K 31/381* (2006.01)

(52) U.S. Cl.
CPC .................. *A61K 31/381* (2013.01)

(58) Field of Classification Search
USPC ........................................................ 514/430
See application file for complete search history.

(56) References Cited

U.S. PATENT DOCUMENTS 7,799,782 B2 * 9/2010 Munson ............... C07D 231/56
514/234.5

FOREIGN PATENT DOCUMENTS

CN        1316904 A       10/2001
EP        2123626 A1      11/2009

OTHER PUBLICATIONS

Matsuoka et al., Anticancer Research., 2012, 32(5): 1805-1810.*
Supriya Bavadekar, et al, "Cytotoxic effects of selective serotonin- and serotonin-norepinephrine reuptake inhibitors on human metastatic breast cancer cell line, MCF-7 (842.3)", FASEB Journal, Apr. 1, 2014, Abstract No. 842.3., cited in Japanese Office Action dated Jun. 5, 2018 of counterpart application No. 2017-522418.
Search Report issued in European counterpart Application No. 15852557.6 by the EPO dated May 30, 2018.

* cited by examiner

*Primary Examiner* — Rei Tsang Shiao
(74) *Attorney, Agent, or Firm* — Hamre, Schumann, Mueller & Larson, P.C.

(57) ABSTRACT

Provided in the present invention are uses of duloxetine hydrochloride in preparing a pharmaceutical composition for treatment of cancer.

7 Claims, 3 Drawing Sheets

USES OF DULOXETINE HCL MEDICAMENT IN PREPARING PHARMACEUTICAL TREATMENT OF CANCER

CROSS-REFERENCE TO RELATED APPLICATION

This application is a bypass continuation of International Application No. PCT/CN2015/092782, filed on Oct. 23, 2015, which claims priority of U.S. Provisional Application No. 62/068,298, filed on Oct. 24, 2014, the entire content of each of which is incorporated herein by reference.

FIELD

The disclosure relates to the application of a duloxetine HCl medicament in a new indication, and more particularly to use of the duloxetine HCl medicament in inhibiting various cancers.

BACKGROUND

Cancer has been the first leading cause of death globally for a long time and the patients suffering from cancer are increasing year by year. Therefore, the treatment of cancer is becoming an important topic. Cancer treatment can be divided into surgical treatment, radiation therapy, chemotherapy and targeted therapy.

Generally, the goal of cancer drug treatment, either chemotherapy or targeted therapy, is mainly to suppress the metastasis and expansion of cancer cells by inhibiting their replication and division.

Cancer drug design also aims at the development of a drug molecule having high specificity or at the design of a targeted antibody. According to statistical data, only about five drugs per ten thousand new drugs are able to access phase I clinical trials.

In addition to the problem of large-scale production of the drugs, other issues that still need to be overcome are drug safety, patient selection and testing dosage, etc. Even if the drug has been approved by the FDA and has been marketed, it is usually the case that a patient's response to the drug is not favorable. Furthermore, many cancer cells may start becoming resistant to the drug, which causes the significant reduction of efficacy of the drug, thereby resulting in failure of the cancer treatment. Therefore, there is a certain level of difficulty with regard to drug development.

Duloxetine hydrochloride (Duloxetine HCl) is a selective serotonin and norepinephrine reuptake inhibitor (SSNRI) for oral administration. The anti-depression mechanism of duloxetine in human bodies is unknown, but it is assumed that such mechanism is associated with the serotonergic and noradrenergic activities of duloxetine acting upon the central nervous system. Pre-clinical tests have shown that duloxetine can effectively block the reuptake of serotonin and norepinephrine, but merely slightly block the reuptake of dopamine. In vitro tests have shown that duloxetine has no significant affinity to dopaminergic, adrenergic, cholinergic or histaminergic receptors. Duloxetine does not inhibit monoamine oxidase. Duloxetine undergoes extensive metabolism, but it has not been found that the major circulating metabolites have significant pharmacologic activity of duloxetine. Duloxetine HCl has been approved by the FDA and there is a large amount of human research result data regarding Duloxetine HCl.

Due to the significant differences in clinical applications, duloxetine HCl has never been considered to have potential to inhibit cancer cells.

SUMMARY

In order to resolve the aforementioned problems, the present invention is directed to the development of the new indication of a duloxetine HCl medicament, thereby achieving the purpose to use the known drug for a new indication.

It is shown via the designed experimental results that the duloxetine HCl medicament has little or no cytotoxicity to the normal cells, and duloxetine HCl exhibits selective effect between normal cells and tumor cells.

The invention provides use of a duloxetine HCl medicament in the manufacture of a pharmaceutical composition for treating cancer, in which the pharmaceutical composition is selected from an effective dosage of duloxetine and a pharmaceutically acceptable salt thereof.

In an embodiment of the present invention, the aforesaid cancer may be one or more cancers selected from thorax-related cancer, peritoneal cavity-related cancer, endocrine-related cancer and digestive tract-related cancer.

In an embodiment of the present invention, the aforesaid cancer may be one or more cancers selected from osteosarcoma-related cancer, skin-related cancer and leukemia-related cancer.

In an embodiment of the present invention, the aforesaid thorax-related cancer may be lung cancer.

In an embodiment of the present invention, the aforesaid peritoneal cavity-related cancer may be selected from bladder cancer and/or cervical cancer.

In an embodiment of the present invention, the aforesaid endocrine-related cancer may be one or more cancers selected from prostate cancer, breast cancer and ovarian cancer.

In an embodiment of the present invention, the aforesaid digestive tract-related cancer may be one or more cancers selected from gastric cancer, liver cancer, colon cancer, pancreatic cancer and lingual cancer.

In an embodiment of the present invention, the effective dosage of the duloxetine HCl medicament may range from 20 mg/kg/day to 500 mg/kg/day.

DETAILED DESCRIPTION

Development of Various Cancer Cell Lines

Figure 1:
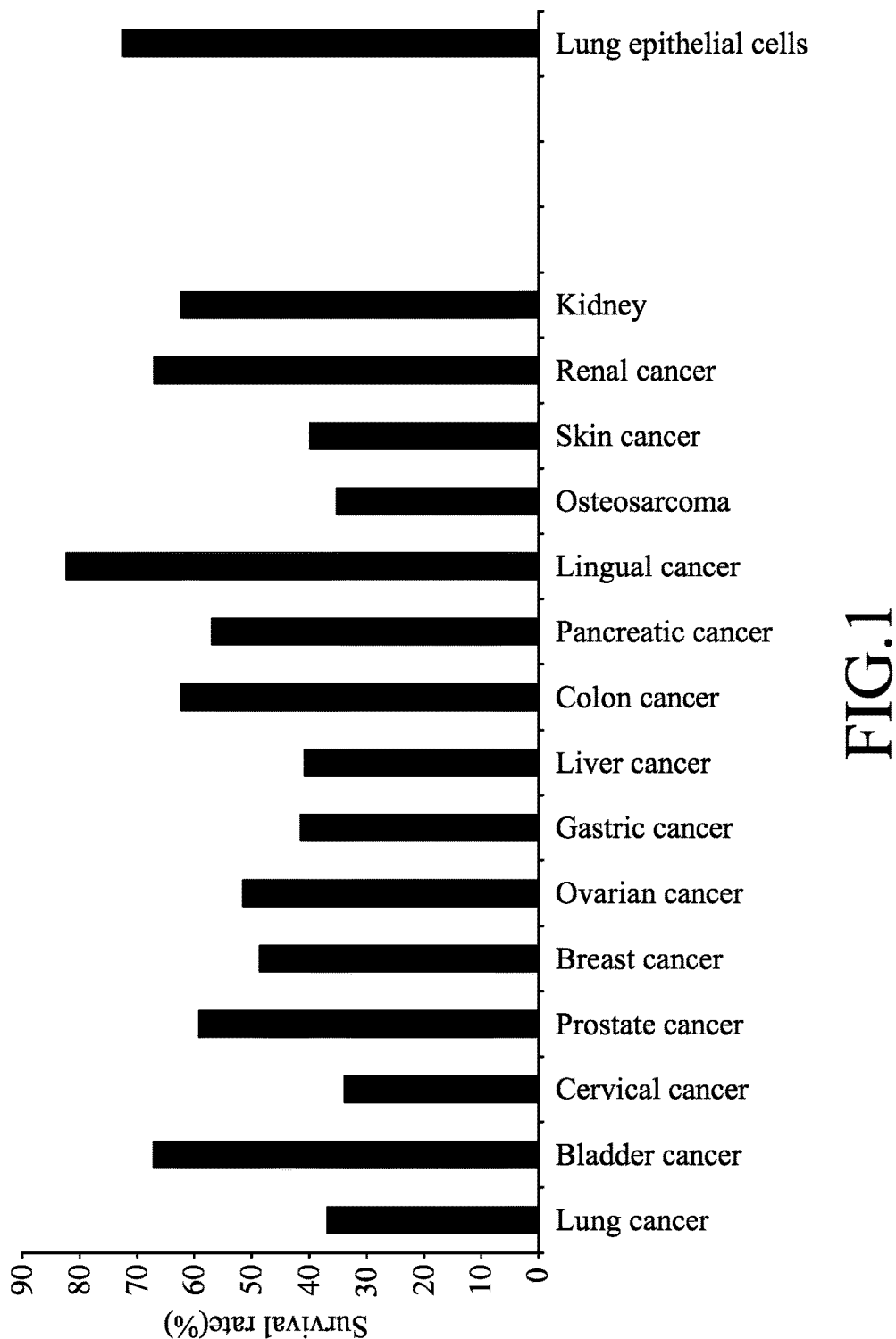
FIG. 1 shows the analysis results of duloxetine HCl of the present invention for use in inhibiting cancer cells.

Different types of cancer cell lines were sub-cultured. These cancer cell types include lung cancer, gastric cancer, liver cancer, colorectal cancer, skin cancer, cervical cancer, prostate cancer, bladder cancer, breast cancer, leukemia, pancreatic cancer, ovarian cancer, lingual cancer, osteosarcoma and renal cancer. The normal cells of the kidney (HEK293) and lung epithelium BEAS-2B serve as the control group to conduct the test (Table 1).

After cultivating each cell in the culture medium (due to different cell characteristics, each of the cancer cell lines was cultivated in the corresponding culture medium (Table 1)), the cell numbers were counted. These cells were seeded at an amount of $2 \times 10^6$ cells, and then added with the culture medium for cultivating the cells to a volume of 10 mL, followed by cultivation for 2 to 3 days. After counting the cell number, these cells were respectively plated in a 96-well plate, in which each well has a fixed cell number of 3000 and a volume of 100 μL.

TABLE 1

Test cancer cell lines and the culture medium for cultivating the same

| No | Cancer | Cancer cell type | Culture medium |
|---|---|---|---|
| 1 | Lung cancer | H1650 (lung adenocarcinoma) | RPMI-1640 |
|   |   | A549 (lung adenocarcinoma) | DMEM |
| 2 | Gastric cancer | AGS (gastric adenocarcinoma) | RPMI-1640 |
|   |   | MKN-45 (gastric adenocarcinoma) | RPMI-1640 |
| 3 | Liver cancer | HepG2 (hepatocellular carcinoma) | DMEM |
|   |   | Hep3B (hepatocellular carcinoma) | DMEM |
| 4 | ColorRectal | HCT116 (p53+) (colorectal carcinoma) | DMEM |
|   |   | LoVo (colorectal adenocarcinoma) | DMEM |
| 5 | Skin cancer | A375 (amelanotic melanoma) | DMEM |
|   |   | BCC (basal cell carcinoma) | DMEM |
| 6 | Cervical cancer | HeLa (cervix adenocarcinoma) | DMEM |
|   |   | C-33A (cervical carcinoma) BCRC 60554 | MEM |
| 7 | Prostate cancer | PC3 (p53−) (prostate adenocarcinoma) | DMEM |
|   |   | LNCaP clone FGC (LNCap.FGC) | RPMI-1640 |
| 8 | Bladder cancer | TSGH (urinary bladder carcinoma) | RPMI-1640 |
|   |   | T24 | RPMI-1640 |
| 9 | Breast cancer | MCF7 (mammary gland, adenocarcinoma) | DMEM |
|   |   | MDA-MB-231 (mammary gland, adenocarcinoma) | DMEM |
| 10 | Pancreatic cancer | BxPC-3 | RPMI-1640 |
|   |   | AsPC-1 | RPMI-1640 |
| 11 | Ovarian cancer | NIH:OVCAR-3 | RPMI-1640 |
|   |   | TOV-21G | RPMI-1640 |
| 12 | Lingual cancer | SAS (tongue squamouscell carcinoma) | DMEM |
| 13 | Osteosarcoma | U-2OS | DMEM |
| 14 | renal cancer | 786-O (renal adenocarcinoma) BCRC 60243 | RPMI-1640 |
| 15 | Normal cell Kidney Lung epithelium | HEK293 (kidney) | DMEM |
|   |   | BEAS-2B (lung epithelial) | RPMI-1640 |

Cell Survival Analysis

After removing the culture medium in the 96-well plate, each well was added with 100 μL of 10 μM commercial drug and then placed for 72 hours. Thereafter, each well was further added with 100 μL of a diluted WST-1 solution (the dilution ratio for the culture medium: WST-1 stock solution (wt/wt) is 9:1). The 96-well plate (each well having a final volume of 200 μL) was placed at 37° C. for 30 to 90 minutes. Absorbance was detected at $OD_{450}$ with an elisa reader (enzyme-linked immunosorbent detector), and the survival rate of each of the cancer cell lines was calculated. A lower survival rate (%) indicates that the drug has a stronger inhibitory effect against the test cancer cell.

Analysis Result of Duloxetine HCl Against Various Cancer Cells

The Test on Inhibitory Effect of Duloxetine HCl Against Thorax-Related Cancer Cells This analysis entitled "The test on inhibitory effect of duloxetine HCl against thorax-related cancer cells" was mainly directed to two types of lung cancer cells, i.e. A549 and H1650 cancer cell lines, for conducting the test. Each cancer cell inhibitory experiment was repeated for 4 times, followed by calculation of the mean values thereof, which were shown in the following table (Table 2).

TABLE 2

The inhibitory test of duloxetine HCl against lung cancer-related cancer cells

|  | 0524-10 min | 0526-10 min | 0529-10 min | 0531-10 min | Mean survival rate (%) |
|---|---|---|---|---|---|
| A549 | 32.8 | 53.7 | 33.2 | 30.1 | 37.5 |
|  | 1-10 min | 2-20 min | 3-20 min | 4-20 min | Mean |
| H1650 | 35.2 | 36.9 | 33.6 | 39.4 | 36.3 |

The Test on Inhibitory Effect of Duloxetine HCl Against Peritoneal Cavity-Related Cancer Cells This analysis entitled "The test on inhibitory effect of duloxetine HCl against peritoneal cavity-related cancer cells" was mainly directed to three types of peritoneal cavity-related cancers for conducting the test. Bladder cancer cell lines were respectively TSGH and T24 cell lines (Table 3). Cervical cancer cell lines were respectively HeLa and C-33A cell lines (Table 4). Renal cancer cell line was 786-O cell line (Table 5). Each cancer cell inhibitory experiment was repeated for 4 times, followed by calculation of the mean values thereof, which were shown in the following tables.

TABLE 3

The inhibitory test of duloxetine HCl against bladder cancer-related cancer cells

| | 0510-10 min | 0512-10 min | 0515-10 min | 0517-10 min | Mean survival rate (%) |
|---|---|---|---|---|---|
| TSGH | 36.1 | 59.0 | 61.2 | 40.5 | 49.2 |
| | T24-1-30 min | T24-2-20 min | T24-3-20 min | T24-4-20 min | Mean |
| T24 | 81.7 | 90.6 | 71.4 | 97.2 | 85.2 |

TABLE 4

The inhibitory test of duloxetine HCl against cervical cancer-related cancer cells

| | 0524-10 min | 0526-10 min | 0529-10 min | 0531-10 min | Mean survival rate (%) |
|---|---|---|---|---|---|
| HeLa | 27.7 | 29.9 | 25.4 | 52.1 | 33.8 |
| C-33A | 34.3 | 52.4 | 33.7 | 42.4 | 40.7 |

TABLE 5

The inhibitory test of duloxetine HCl against renal cancer-related cancer cells

| | 0524-10 min | 0526-10 min | 0529-10 min | 0531-10 min | Mean survival rate (%) |
|---|---|---|---|---|---|
| 786-O | 60.4 | 89.7 | 49.0 | 70.1 | 67.3 |

The Test on Inhibitory Effect of Duloxetine HCl Against Endocrine-Related Cancer Cells This analysis entitled "The test on inhibitory effect of duloxetine HCl against endocrine-related cancer cells" was mainly directed to three types of endocrine-related cancers for conducting the test. Prostate cancer cell lines were respectively PC-3 and LNCap cell lines (Table 6). Breast cancer cell lines were respectively MCF-7 and MDA-MB-231 cell lines (Table 7). Ovarian cancer cell lines were respectively NIH-OVCAR-3 and TOV-21G cell lines (Table 8). Each cancer cell inhibitory experiment was repeated for 4 times, followed by calculation of the mean values thereof, which were shown in the following tables.

TABLE 6

The inhibitory test of duloxetine HCl against prostate cancer-related cancer cells

| | PC-3-0524-10 min | PC-3-0526-10 min | PC-3-0529-10 min | PC-3-0531-10 min | Mean survival rate (%) |
|---|---|---|---|---|---|
| PC-3 | 45.0 | 70.9 | 41.4 | 25.1 | 45.6 |
| | | | | | Mean |
| LNCap | | | | | 72.8 |

TABLE 7

The inhibitory test of duloxetine HCl against breast cancer-related cancer cells

| | 0612-10 min | 0614-10 min | 0616-10 min | 0619-10 min | Mean survival rate (%) |
|---|---|---|---|---|---|
| MCF-7 | 29.0 | 37.3 | 30.0 | 28.5 | 31.2 |
| | 0612-10 min | 0614-10 min | 0616-10 min | | Mean |
| MDA-MB-231 | 53.4 | 70.2 | 74.3 | | 65.9 |

TABLE 8

The inhibitory test of duloxetine HCl against ovarian cancer-related cancer cells

| | 7-3-30 min | 7-4-30 min | 7-7-30 min | -4-30 min | Mean survival rate (%) |
|---|---|---|---|---|---|
| NIH-OVCAR-3 | 64.8 | 74.6 | 78.5 | 55.0 | 68.2 |
| | 7-3-30 min | 7-4-30 min | 7-7-30 min | -4-30 min | Mean |
| TOV-21G | 30.9 | 41.9 | 34.7 | 31.9 | 34.9 |

The Test on Inhibitory Effect of Duloxetine HCl Against Digestive Tract-Related Cancer Cells This analysis entitled "The test on inhibitory effect of duloxetine HCl against digestive tract-related cancer cells" was mainly directed to five types of digestive tract-related cancers for conducting the test. Gastric cancer cell lines were respectively AGS and MKN-45 cell lines (Table 9). Liver cancer cell lines were respectively HepG2 and Hep3B cell lines (Table 10). Colorectal cancer cell lines were respectively HCT116-wt and LoVo cell lines (Table 11). Pancreatic cancer cell lines were respectively AsPC-1 and BxPC-3 cell lines (Table 12). Lingual cancer cell line was SAS cell line (Table 13). Each cancer cell inhibitory experiment was repeated for 4 times, followed by calculation of the mean values thereof, which were shown in the following tables.

TABLE 9

The inhibitory test of duloxetine HCl against gastric cancer-related cancer cells

| | 0510-10 min | 0512-10 min | 0515-10 min | 0517-10 min | Mean survival rate (%) |
|---|---|---|---|---|---|
| AGS | 25.0 | 15.9 | 37.3 | 15.8 | 23.5 |
| | 0510-10 min | 0512-10 min | 0515-10 min | 0517-10 min | Mean |
| MKN-45 | 59.5 | 75.3 | 46.0 | 57.9 | 59.7 |

TABLE 10

The inhibitory test of duloxetine HCl against liver cancer-related cancer cells

| | 0524-20 min | 0526-20 min | 0529-20 min | 0531-20 min | Mean survival rate (%) |
|---|---|---|---|---|---|
| HepG2 | 14.8 | 44.7 | 37.7 | 38.9 | 34.0 |

| | 0612-20 min | 0614-20 min | 0616-20 min | 0619-20 min | Mean |
|---|---|---|---|---|---|
| Hep3B | 41.4 | 53.3 | 36.2 | 60.6 | 47.9 |

TABLE 11

The inhibitory test of duloxetine HCl against colorectal cancer-related cancer cells

| | 0602-30 min | 0605-10 min | 0607-10 min | 0609-10 min | Mean survival rate (%) |
|---|---|---|---|---|---|
| HCT116-wt | 52.1 | 108.8 | 127.4 | 20.3 | 77.1 |

| | 0616-10 min | 0619-10 min | 0621-10 min | 0623-10 min | Mean survival rate (%) |
|---|---|---|---|---|---|
| LoVo | 44.8 | 63.4 | 49.9 | 31.0 | 47.3 |

TABLE 12

The inhibitory test of duloxetine HCl against pancreatic cancer-related cancer cells

| | 1-7-3-30 min | 1-7-4-30 min | 1-7-7-30 min | 1-4-30 min | Mean survival rate (%) |
|---|---|---|---|---|---|
| AsPC-1 | 75.7 | 78.0 | 26.0 | 61.7 | 60.3 |

| | 3-7-3-30 min | 3-7-4-30 min | 3-7-7-30 min | 3-4-30 min | Mean survival rate (%) |
|---|---|---|---|---|---|
| BxPC-3 | 62.1 | 58.8 | 22.7 | 72.4 | 54.0 |

TABLE 13

The inhibitory test of duloxetine HCl against lingual cancer-related cancer cells

| | 6-26-10 min | 6-28-10 min | 6-30-10 min | 7-3-10 min | Mean survival rate (%) |
|---|---|---|---|---|---|
| SAS | 45.7 | 88.9 | 96.2 | 98.9 | 82.4 |

The Test on Inhibitory Effect of Duloxetine HCl Against Other Cancer Cells

The analysis of duloxetine HCl against other types of cancers was performed. Osteosarcoma cell line was U2OS cell line (Table 14). Skin cancer cell lines were respectively A375 and BCC cell lines (Table 15). Each cancer cell inhibitory experiment was repeated for 3 or 4 times, followed by calculation of the mean values thereof, which were shown in the following tables.

TABLE 14

The inhibitory test of duloxetine HCl against osteosarcoma-related cancer cells

| | 6-26-10 min | 6-28-10 min | 6-30-10 min | 7-3-10 min | Mean survival rate (%) |
|---|---|---|---|---|---|
| U2OS | 26.6 | 21.5 | 56.6 | 35.6 | 35.1 |

TABLE 15

The inhibitory test of duloxetine HCl against skin cancer-related cancer cells

| | 0602-30 min | 0605-10 min | 0607-10 min | 0609-10 min | Mean survival rate (%) |
|---|---|---|---|---|---|
| A375 | 25.7 | 16.2 | 17.1 | 67.0 | 31.5 |

| | 0602-30 min | 0605-10 min | 0607-10 min | Mean |
|---|---|---|---|---|
| BCC | 43.9 | 31.3 | 69.0 | 48.1 |

Experimental Design for Control Group

The Test on Inhibitory Effect of Duloxetine HCl Against Normal Cells

The analysis of duloxetine HCl against many types of normal cells was performed. Normal kidney cell line was HEK293 cell line (Table 16). Normal lung epithelial cell line was BEAS-2B cell line (Table 17). Each cell inhibitory experiment was repeated for 4 times, followed by calculation of the mean values thereof, which were shown in the following tables.

TABLE 16

The inhibitory test of duloxetine HCl against normal kidney cells

| | Mean survival rate (%) |
|---|---|
| HEK 293 | 62.4 |

TABLE 17

The inhibitory test of duloxetine HCl against normal lung epithelial cells

| | 0510-10 min | 0512-10 min | 0515-10 min | 0517-10 min | Mean survival rate (%) |
|---|---|---|---|---|---|
| BEAS-2B | 59.5 | 76.3 | 74.7 | 79.6 | 72.5 |

The inhibitory effect of duloxetine HCl against various cancer cells was tabulated in Table 18. It can be clearly seen that duloxetine HCl exhibits significant inhibitory effect against various cancers. It is noted from the inventors' experimental results that duloxetine HCl may have significant inhibitory effects against various cancer cells (see FIG. 1).

TABLE 18

Summary of inhibitory test of duloxetine HCl against various cancer cells

| Cancer cells | Survival rate (%) |
|---|---|
| Lung cancer | 36.8743253 |
| Bladder cancer | 67.2 |
| Cervical cancer | 36.76 |
| Prostate cancer | 59.23 |
| Breast cancer | 48.57 |
| Ovarian cancer | 51.5 |
| Gastric cancer | 41.6 |
| Liver cancer | 40.95 |
| Colorectal cancer | 62.21 |
| Pancreatic cancer | 57.2 |
| Lingual cancer | 82.44 |
| Osteosarcoma | 35.09 |

TABLE 18-continued

Summary of inhibitory test of duloxetine HCl against various cancer cells

| Cancer cells | Survival rate (%) |
|---|---|
| Skin cancer | 39.79 |
| Renal cancer | 67.3 |
| Kidney | 62.44 |
| Lung epithelial cells | 72.50 |

Animal Experimental Analysis

This experiment was performed with female BALB/cAnN.Cg-Foxn1nu/CrlNarl mice with a weight of around 21±1 gas samples. After subcutaneous injection of liver cancer cells (HepG2), the mice were randomly divided into three groups based on the test drug, i.e., normal control group, low dosage group (100 mg/kg/day) and high dosage group (200 mg/kg/day). After the tumor was grown to be over 100 mm$^3$, the mice were treated with the drug via intraperitoneal injection daily. The tumor size was measured two times per week. The formula for determining the tumor size was as follows: $(L \times W^2)/2$, in which L represents the longest diameter of the tumor and W represents the shortest diameter of the tumor.

TABLE 19

The inhibitory test of duloxetine HCl against cancers in animal experiments

| | Control group | | | | | Low dosage (100 mg/kg/day) | | |
|---|---|---|---|---|---|---|---|---|
| | Weight (g) | L (mm) | W (mm) | Volume (mm$^3$) | Increased tumor volume (mm$^3$) | Weight (g) | L (mm) | W (mm) |
| *First measurement* | | | | | | | | |
| A | 18.5 | 7 | 7 | 171.5 | 171.5 | 19 | 7 | 5 |
| B | 22 | 8 | 6 | 144 | 144 | 19 | 8 | 6 |
| C | 20.5 | 9 | 8 | 288 | 288 | 18 | 6 | 6 |
| Mean | | | | 201.1667 | 201.1667 | | | |
| *Second measurement* | | | | | | | | |
| A | 22 | 7 | 6 | 126 | −45.5 | 19 | 6 | 5 |
| B | 20 | 8 | 7 | 196 | 52 | 21 | 7 | 6 |
| C | 20 | 9 | 7 | 220.5 | −67.5 | 20 | 7 | 6 |
| Mean | | | | 180.8333 | −20.3333 | | | |
| *Third measurement* | | | | | | | | |
| A | 23 | 9 | 6 | 162 | 36 | 20.5 | 7 | 6 |
| B | 20 | 10 | 8 | 320 | 124 | 23.5 | 7 | 4 |
| C | 21 | 11 | 7 | 269.5 | 49 | 19 | 7 | 5 |
| Mean | | | | 250.5 | 69.66667 | | | |
| *Fourth measurement* | | | | | | | | |
| A | 23 | 11 | 7 | 269.5 | 107.5 | 22 | 6 | 6 |
| B | 22 | 10 | 6 | 180 | −140 | 22 | 4 | 4 |
| C | 23 | 11 | 8 | 352 | 82.5 | 20 | 6 | 5 |
| Mean | | | | 267.1667 | 16.66667 | | | |
| *Fifth measurement* | | | | | | | | |
| A | 22 | 12 | 8 | 384 | 114.5 | 22 | 6 | 6 |
| B | 22 | 11 | 8 | 352 | 172 | 20 | 4 | 5 |
| C | 23 | 12 | 9 | 486 | 134 | 20 | 4 | 4 |
| Mean | | | | 407.3333 | 140.1667 | | | |

| Low dosage (100 mg/kg/day) | | High dosage (200 mg/kg/day) | | | | |
|---|---|---|---|---|---|---|
| Volume (mm$^3$) | Increased tumor volume (mm$^3$) | Weight (g) | L (mm) | W (mm) | Volume (mm$^3$) | Increased tumor volume (mm$^3$) |

TABLE 19-continued

The inhibitory test of duloxetine HCl against cancers in animal experiments

First measurement

| | | | | | | | |
|---|---|---|---|---|---|---|---|
| A | 87.5 | 87.5 | 19 | 6 | 4 | 48 | 48 |
| B | 144 | 144 | 18.5 | 8 | 5 | 100 | 100 |
| C | 108 | 108 | 20 | 7 | 5 | 87.5 | 87.5 |
| Mean | 113.1667 | 113.1667 | | | | 78.5 | 78.5 |

Second measurement

| | | | | | | | |
|---|---|---|---|---|---|---|---|
| A | 75 | −12.5 | 20 | 6 | 4 | 48 | 0 |
| B | 126 | −18 | 23 | 5 | 3 | 22.5 | −77.5 |
| C | 126 | 18 | 20 | 7 | 5 | 87.5 | 0 |
| Mean | 109 | −4.16667 | | | | 52.66667 | −25.8333 |

Third measurement

| | | | | | | | |
|---|---|---|---|---|---|---|---|
| A | 126 | 51 | 19 | 5 | 4 | 40 | −8 |
| B | 56 | −70 | 18.5 | 0 | 0 | 0 | −22.5 |
| C | 87.5 | −38.5 | 18.5 | 0 | 0 | 0 | −87.5 |
| Mean | 89.83333 | −19.1667 | | | | 13.33333 | −39.3333 |

Fourth measurement

| | | | | | | | |
|---|---|---|---|---|---|---|---|
| A | 108 | −18 | 20 | 0 | 0 | 0 | −40 |
| B | 32 | −24 | 21 | 0 | 0 | 0 | 0 |
| C | 75 | −12.5 | 20 | 0 | 0 | 0 | 0 |
| Mean | 71.66667 | −18.1667 | | | | 0 | −13.3333 |

Fifth measurement

| | | | | | | | |
|---|---|---|---|---|---|---|---|
| A | 108 | 0 | 21 | 0 | 0 | 0 | 0 |
| B | 50 | 18 | 20 | 0 | 0 | 0 | 0 |
| C | 32 | −43 | 20 | 0 | 0 | 0 | 0 |
| Mean | 63.33333 | −8.33333 | | | | 0 | 0 |

Figure 2:
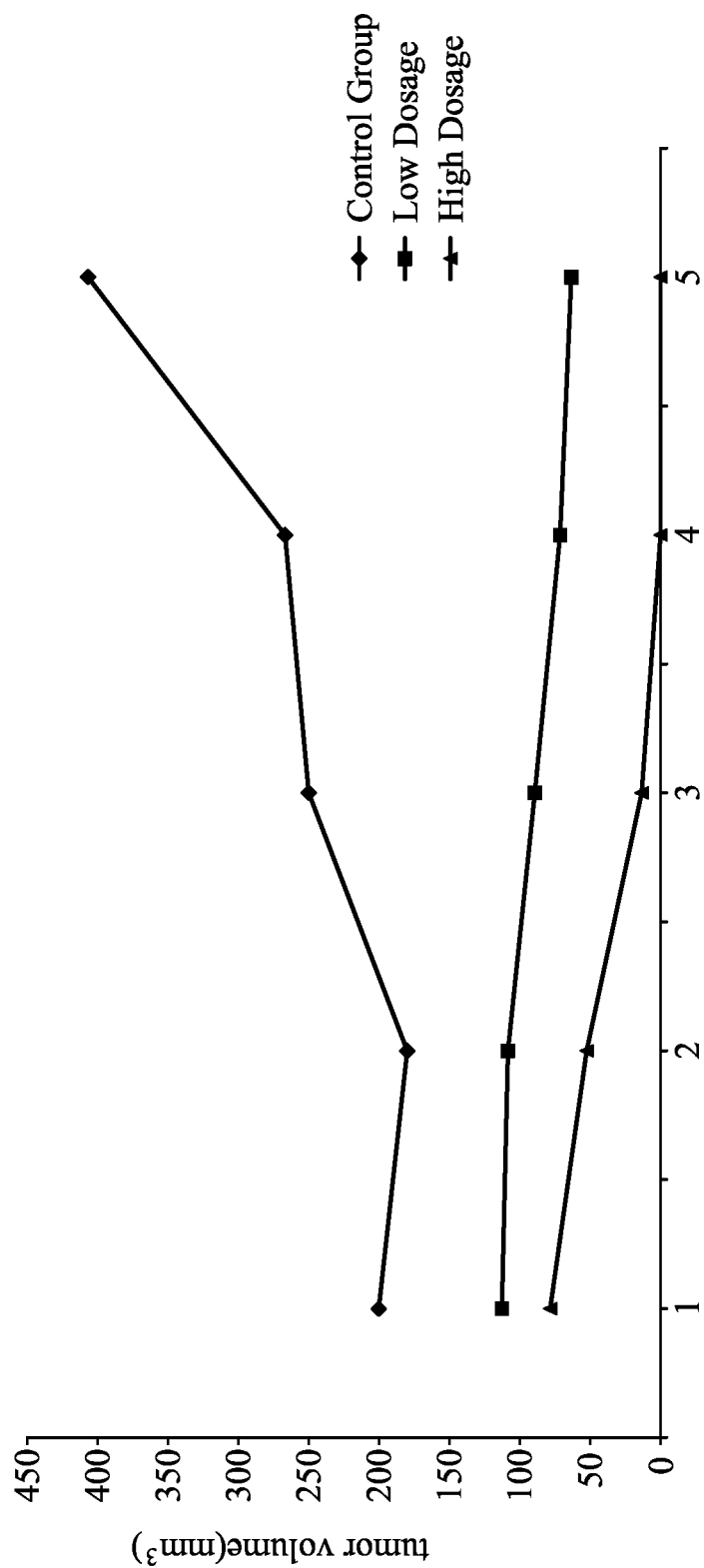
FIG. 2 shows the effect of duloxetine HCl on tumor volume.

According to the result of FIG. 2, both low dosage and high dosage of duloxetine HCl have great inhibitory effect against the tumors. There was no obvious weight loss in each group of mice during the experiments. It thus indicates that duloxetine HCl, either high or low dosage, may let the test mice be in optimal health conditions and not die during the treatment.

Figure 3:
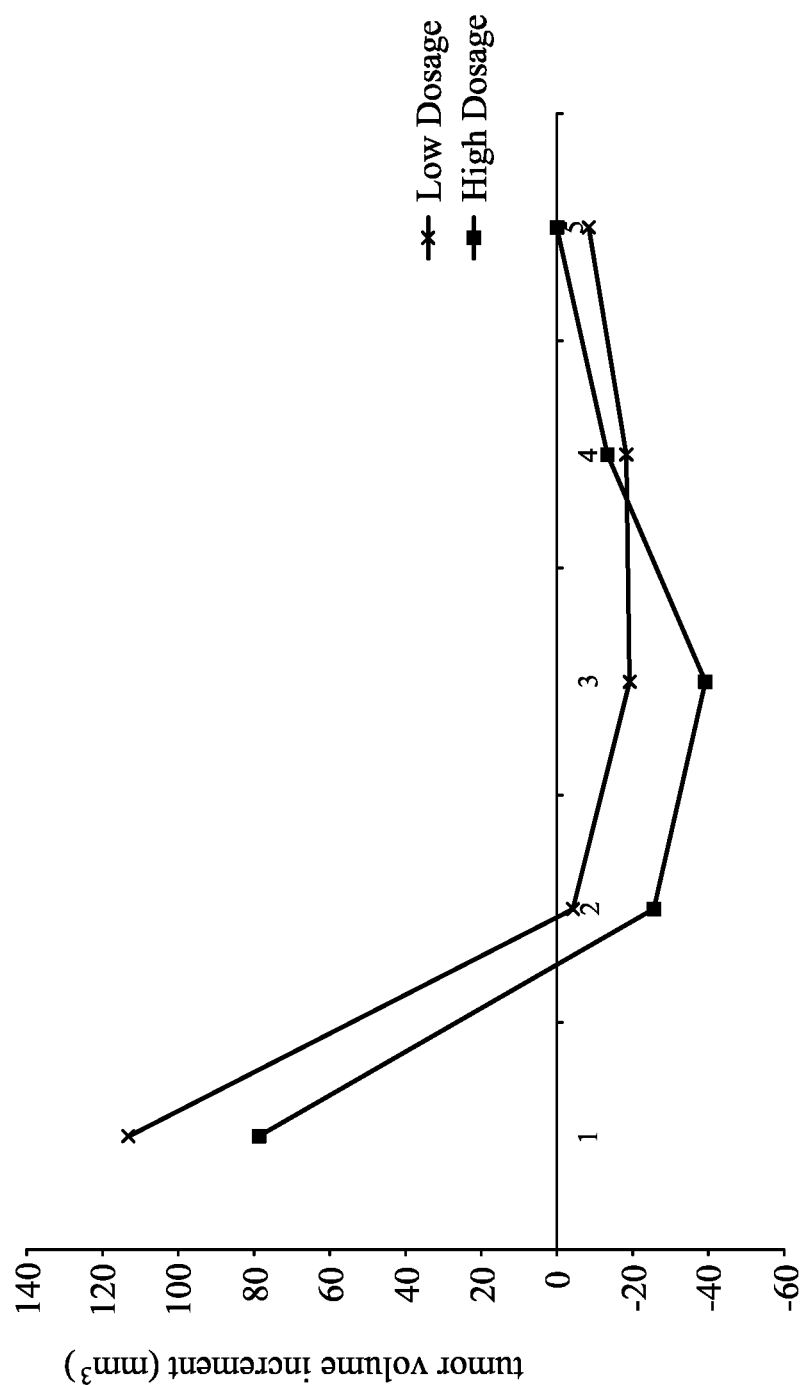
FIG. 3 shows the inhibitory effect of duloxetine HCl in high dosage and low dosage on tumor growth.

According to the result of FIG. 3, low dosage and high dosage of duloxetine HCl may effectively inhibit the increase of tumor volume, and meanwhile decrease the tumor volume. In particular, high dosage of duloxetine HCl has a better effect.

The detailed description above serves to illustrate the practicable embodiment (s) of the present disclosure. However, such embodiment (s) cannot be utilized to limit the claimed scope of the present disclosure. Accordingly, the claimed scope of the present disclosure is intended to encompass all equivalent practice or changes without departing from the spirit of the invention.

What is claimed is:

1. A method for treating cancer in a subject, comprising administering to the subject an effective amount of duloxetine or a pharmaceutically acceptable salt thereof,
    wherein the cancer is at least one cancer selected from the group consisting of thorax-related cancer, peritoneal cavity-related cancer, endocrine-related cancer, digestive tract-related cancer, osteosarcoma, skin cancer, and leukemia, and
    cell growth of the cancer is inhibited by the duloxetine or the pharmaceutically acceptable salt thereof.

2. The method of claim 1, wherein the thorax-related cancer is lung cancer.

3. The method of claim 1, wherein the peritoneal cavity-related cancer is selected from the group consisting of bladder cancer and cervical cancer.

4. The method of claim 1, wherein the endocrine-related cancer is selected from the group consisting of prostate cancer, breast cancer and ovarian cancer.

5. The method of claim 1, wherein the digestive tract-related cancer is selected from the group consisting of gastric cancer, liver cancer, colorectal cancer, pancreatic cancer, and lingual cancer.

6. The method of claim 1, wherein the effective amount of duloxetine or the pharmaceutically acceptable salt thereof ranges from 20 mg/kg/day to 500 mg/kg/day.

7. The method of claim 1, wherein the pharmaceutical acceptable salt of duloxetine is duloxetine HCl.

* * * * *